US00RE40472E

(19) United States
(12) Reissued Patent
Bolmsjö

(10) Patent Number: US RE40,472 E
(45) Date of Reissued Patent: Aug. 26, 2008

(54) METHOD AND DEVICE FOR COMBINED HEAT TREATMENT OF BODY TISSUE

(75) Inventor: Magnus Bolmsjö, Lund (SE)

(73) Assignee: ProstaLund Operations AB, Lund (SE)

(21) Appl. No.: 10/816,377

(22) Filed: Apr. 1, 2004

Related U.S. Patent Documents

Reissue of:
(64) Patent No.: 6,366,818
Issued: Apr. 2, 2002
Appl. No.: 09/379,424
Filed: Aug. 23, 1999

U.S. Applications:
(63) Continuation-in-part of application No. PCT/SE98/01417, filed on Jul. 28, 1998.

(30) Foreign Application Priority Data

Feb. 4, 1999 (SE) ..... 9900382

(51) Int. Cl.
*A61F 2/00* (2006.01)

(52) U.S. Cl. ..... 607/102
(58) Field of Classification Search ..... 606/41–50, 606/33; 607/96–102, 116, 156
See application file for complete search history.

(56) References Cited

U.S. PATENT DOCUMENTS

| | | | |
|---|---|---|---|
| 4,204,549 | A | 5/1980 | Paglion |
| 4,311,154 | A | 1/1982 | Sterzer et al. |
| 4,535,773 | A | 8/1985 | Yoon |
| 4,676,258 | A | 6/1987 | Inokuchi et al. |
| 4,754,752 | A | 7/1988 | Ginsburg et al. |
| 4,860,744 | A | 8/1989 | Johnson et al. |
| 4,949,718 | A | 8/1990 | Neuwirth et al. |
| 4,967,765 | A | 11/1990 | Turner et al. |
| 4,979,948 | A | 12/1990 | Geddes et al. |
| 5,007,437 | A | 4/1991 | Sterzer |
| 5,007,897 | A | 4/1991 | Kalb et al. |
| 5,084,044 | A | 1/1992 | Quint |
| 5,103,804 | A | 4/1992 | Abele et al. |

(Continued)

FOREIGN PATENT DOCUMENTS

| | | |
|---|---|---|
| EP | 0370890 | 5/1990 |
| EP | 0449472 | 10/1991 |
| EP | 0462302 | 12/1991 |
| JP | 55166148 | 1/1980 |
| JP | 2121675 | 5/1990 |
| JP | 576611 | 1/1993 |
| JP | 767908 | 1/1995 |
| SE | 9502523-5 | 6/1987 |
| WO | WO91/17731 | 11/1991 |
| WO | WO93/09724 | 5/1993 |
| WO | WO94/01177 | 1/1994 |
| WO | WO95/19142 | 7/1995 |
| WO | WO96/36288 | 11/1996 |
| WO | WO97/02794 | 1/1997 |
| WO | WO99/07325 | 2/1999 |
| WO | WO99/17689 | 4/1999 |
| WO | WO00/45758 | 8/2000 |

OTHER PUBLICATIONS

Jozef Mendecki, Ph.D., et al., *Microwave Applicators for Localized Hypertherma Treatment of Cancer of the Prostrate,* Technical Innovations and Notes, Nov. 1980, vol. 6, No. 11, pp. 1583 through 1588.

*Primary Examiner*—Roy D Gibson
(74) *Attorney, Agent, or Firm*—John R. Ley

(57) ABSTRACT

The invention relates to a method and a device for heat treatment of prostatic tissue. The device comprises a treatment catheter with an expandable fluid reservoir and first heating means which is arranged within the treatment catheter and emits electromagnetic radiation for heating of the surrounding prostatic tissue. A second heating means is provided in thermal contact with the liquid in the fluid reservoir for heating of the liquid in the fluid reservoir as well as the tissue located in the immediate surrounding of the reservoir.

108 Claims, 4 Drawing Sheets

U.S. PATENT DOCUMENTS

| | | | |
|---|---|---|---|
| 5,159,925 | A | 11/1992 | Neuwirth et al. |
| 5,222,938 | A | 6/1993 | Behl |
| 5,222,953 | A | 6/1993 | Dowlatshahi |
| 5,234,004 | A | 8/1993 | Hascoet et al. |
| 5,257,977 | A | 11/1993 | Eshel |
| 5,334,206 | A | 8/1994 | Daikuzono |
| 5,344,435 | A | 9/1994 | Turner et al. |
| 5,366,490 | A | 11/1994 | Edwards et al. |
| 5,368,591 | A | 11/1994 | Lennox et al. |
| 5,370,676 | A | 12/1994 | Sozanski et al. |
| 5,421,819 | A | 6/1995 | Edwards et al. |
| 5,464,445 | A | 11/1995 | Rudie et al. |
| 5,480,417 | A | 1/1996 | Hascoet et al. |
| 5,492,529 | A | 2/1996 | Neuwirth et al. |
| 5,496,271 | A | 3/1996 | Burton et al. |
| 5,500,012 | A | 3/1996 | Brucker et al. |
| 5,540,679 | A | 7/1996 | Fram et al. |
| 5,578,008 | A | 11/1996 | Hara |
| 5,623,940 | A | 4/1997 | Daikuzono |
| 5,645,528 | A | 7/1997 | Thome |
| 5,681,282 | A | 10/1997 | Eggers et al. |
| 5,800,432 | A | 9/1998 | Swanson |
| 5,843,144 | A | 12/1998 | Rudie et al. |
| 5,861,021 | A | 1/1999 | Thome et al. |
| 5,902,251 | A | 5/1999 | vanHooydonk |
| 5,931,860 | A | 8/1999 | Reid et al. |
| 5,964,791 | A | 10/1999 | Bolmsjö |
| 6,002,968 | A | 12/1999 | Edwards |
| 6,223,085 | B1 | 4/2001 | Dann et al. |
| 6,496,737 | B2 | 12/2002 | Rudie et al. |

METHOD AND DEVICE FOR COMBINED HEAT TREATMENT OF BODY TISSUE

Matter enclosed in heavy brackets [ ] appears in the original patent but forms no part of this reissue specification; matter printed in italics indicates the additions made by reissue.

*CROSS REFERENCE TO RELATED APPLICATIONS*

*This is a continuation in part of international application PCT/SE98/01417, filed Jul. 28, 1998, which designated the United States and for which a demand for international preliminary examination was timely made, and of U.S. application Ser. No. 08/981,878, filed Jan. 6, 1998, both of which are now abandoned.*

TECHNICAL FIELD OF THE INVENTION

The invention concerns a method and device for heat treatment of bodily tissue.

Heat treatment yields good treatment results with certain types of disease conditions involving unnatural growth of tissue. The tissue is heated to the extent that it dies. Examples of such disease conditions are certain types of cancer and benign prostate hyperplasy, BPII. During treatment certain portions of the tissue are heated so that tissue death ensues, while other portions of tissue must or should be protected. The disease conditions which are primarily indicated are those which occur in tissue surrounding cavities in the body.

Corresponding disease conditions can also occur in animals, where corresponding treatment can be brought to bear. Above all, treatment of the prostate in domestic animals, such as dogs, can be topical.

STATE OF THE ART

Different devices can be used in order to induce heating. Devices for heating by means of laser as well as with microwaves and radio frequencies are common. A technique is known through U.S. Pat. No. 5,257,977, according to which a catheter is provided with a reservoir for fluid. The reservoir is flexible and is connected via channels through the catheter with a heating device located outside the body. A fluid is heated in a heating device and circulated through the channels and the reservoir that to some degree expands for better contact with the tissue. The rise of temperature in the reservoir also brings about heating of the surrounding tissue. Treatment is affected by controlling the temperature of the circulating fluid.

Since the channels pass through tissue that should not be treated, they must be heat insulated. According to U.S. Pat. No. 5,257,977 the heat insulation is brought about by means of a space filled with gas that surrounds the channels. The function of the heat insulation is very important, for which reason great care and considerable expense must be devoted to this part of the treatment catheter. Another disadvantage with the device according to U.S. Pat. No. 5,257,977 is that desired control of the temperature is difficult to achieve for the reason that the distance between the heating device and the area of treatment is relatively large and because the temperature of the circulating fluid should not exceed 140° F. (60° C.) in order to avoid an effect on the urethra outside of the prostate and penis brought about by heat in the in/out channels.

A more highly developed catheter for treatment is shown and described in WO 97/02794, according to which a heating device is contained inside an expandable reservoir. The heating device is provided with energy from an assembly outside of the body for heating of fluid inside the reservoir. Some of the disadvantages involving undesirable heating of certain tissue are avoided in this manner. The heating device is designed according to WO 97/02794 as a resistance wire or similar and heats the fluid through convection. The heat transferred from the fluid to the surrounding tissue gives locally good results. A disadvantage is that the effect in the tissue at a farther distance from the reservoir is insignificant, for which reason the volume of tissue that can be treated is limited with this technique.

Heat treating with a treatment catheter that is equipped with a microwave antenna is also known with the mentioned course of disease. Examples of such microwave treatment are known previously through U.S. Pat. No. 5,480,417 and U.S. Pat. No. 5,234,004. Characteristic for previously known microwave treatment is that the prostate tissue is heated with microwaves. The intention is to heat parts of the prostate gland. The element that emits the microwave radiation consists of a coaxial cable that is included in a catheter for treatment. Cooling fluid circulates through the catheter. The intention with the cooling is to protect the prostatic urethra, that is to say the part of the urethra that runs through the prostate gland from being affected and damaged by the heat that is generated by the microwaves. Another reason for cooling the catheter is to transport away waste heat in the coaxial cable.

In several of these previously known techniques cited earlier the goal of the treatment was not made explicit but it was rather merely indicated that the invention should be used for heat treatment of the prostate. Different levels of heat treatments occur in the literature. So-called hyperthermy treatments have in general the goal only to increase the temperature moderately, <113° F.; 45° C. It is known that histological changes in tissue do not occur with temperatures less than 113° F. (45° C.) and that the temperature must exceed 122° F. (50° C.) in order to achieve destruction of tissue in a short time, on the order of one hour or less. In connection with the described invention heat treatment is meant to have such a high temperature that the tissue coagulates, i.e., dies.

It has long been viewed as important to protect the prostatic urethra during microwave treatment of benign prostate enlargement. This protection of the prostatic urethra hinders the treatment from being really effective, however, since parts of the obstructing tissue closest to the urethra are not heated sufficiently in order to coagulate because of the cooling. Neither are there any medicinal-scientific attestations that non-destruction of the prostatic urethra should be preferred. To the contrary it can be argued that destruction of the prostatic urethra along with other tissue means that necroticized tissue is not encapsulated but is naturally discharged with urine during the healing process. The clinical result of heat treatment of the kind envisioned here is dependent on the amount of tissue that coagulates. The degree of coagulation depends in turn on temperature in combination with the length of treatment. The temperature in turn depends on the input of energy and the carrying away of heat by the blood flow. Since different parts of the prostate can have different degrees of blood flow, there is a risk that certain areas will not achieve therapeutic temperature when micowaves are used for heating.

There are also designs with uncooled catheters for treatment. In these the microwave power has been so low that the tissue temperature has not been sufficient to achieve coagulation. Because of cable losses the development of heat in the feed cable (coaxial cable) itself that transmits microwaves through the urethra to the prostate is so hihg that uncooled catheters can be used only with low microwave power, for example 20 watts. This magnitude is insufficient to bring about tissue necrosis in the prostate and produces only an insignificant heating of the tissue. Equipment of this kind also yields generally poor objective treatment results.

THE INVENTION IN SUMMARY

A purpose of the invention is to increase the effectiveness of treatment with a treatment catheter of previously known technology at the same time as to diminish the risk of maltreatment of tissue. The diminution of risk depends among other things on decreasing the amount of microwave power applied in comparison with known technology. The duration of treatment can also be shortened many times with the invention shown in comparison with known technology. According to preferred embodiments it will also be possible partly to treat tissue far from the prostatic urethra and partly to secure destruction of the prostatic urethra itself and the surrounding area in a controlled way. This purpose is achieved by incorporation of the special features described in patent claims 1 and 12, respectively.

The effectiveness of treatment is increased in that a device for treatment according to the invention comprises means developed to expand the treatment catheter in the longitudinal direction from the apex of the photostat or beyond all the way up to and including the base of the bladder. The cavity that is constituted by the prostatic urethra is filled by a bolus or reservoir filled with fluid so that a good fit occurs between the treatment catheter and the tissue. Separate devices for treating the tissue around the prostatic urethra and more distant tissue are included. Through this means it is possible to control the supply of power in a better way, which increases safety for the patient and diminishes the risk of damage caused by the treatment as a result of hihg total power output.

Further advantages and special features of the invention emerge from the following description, drawings, and dependent patent claims.

BRIEF DESCRIPTION OF THE DRAWINGS

The invention will now be described in more detail with the aid of examples of embodiments with reference to the attached drawings on which.

THE INVENTION

Figure 1:
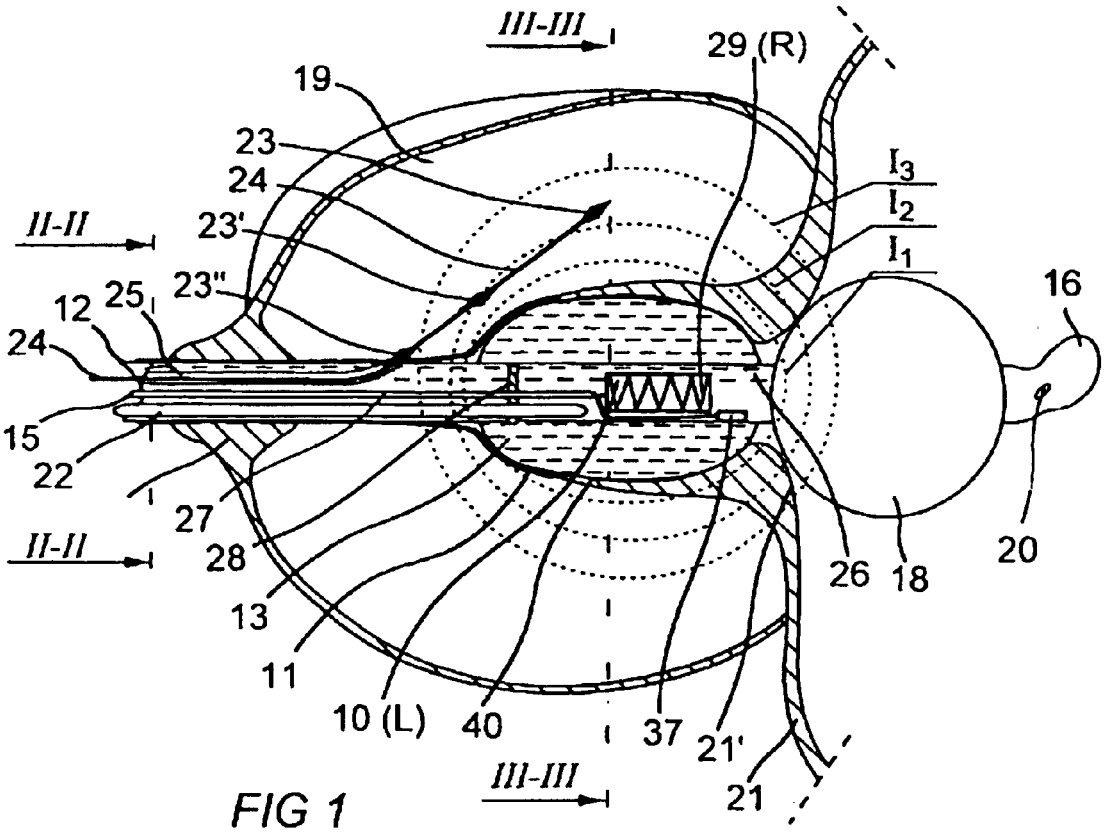
FIG. 1 is a principal cross-sectional view in the longitudinal direction of an embodiment of a treatment catheter according to the invention.

In the embodiment of a treatment catheter according to the invention shown in FIG. 1 a fluid reservoir 11 is arranged externally on a treatment catheter 12. The treatment catheter is intended primarily for treatment of prostate tissue. Fluid reservoir 11 is elastic and in FIG. 1 is expanded by introduction of fluid 13 into it. When fluid is introduced into reservoir 11, it expands and fills the cavity constituted by the prostatic urethra. Contact between reservoir 11 and the prostatic tissue is good.

Treatment catheter 12 according to FIG. 1 is introduced through the urethra so that tip 16 extends into urinary bladder 21. A bladder or balloon 18 connected with the treatment catheter is expanded inside urinary bladder 21 and prevents unintended withdrawal of the treatment catheter during the process of treatment. The active part of the treatment catheter is thus centrally located in the tissue that is to be treated, in this case in prostate 19. The treatment catheter 12 is flexible and pliable in order to be introduced flexibly through the urethra to the treatment position.

Urinary bladder 21 is connected via bladder neck 21' into the urethra. As can be seen in FIG. 1, the bladder neck 21' is expanded along with the upper part of the prostatic urethra when fluid reservoir 11 is expanded, whereby good contact with the tissue is maintained. This is favorable for many reasons. Bladder neck 21' and the surrounding tissue can often have a different flow-through of blood than other parts of the prostate. The blood flow-through leads to heat being conducted away from the treatment area so that the resulting temperature of the tissue is different in the opening to the urethra in comparison with central parts of the prostate.

A first heating device 10 is arranged inside treatment catheter 12 for heating of the surrounding tissue. First heating device 10 emits electromagnetic radiation, preferably in the form of microwaves. First heating device 10 preferably comprises a microwave antenna. Energy emitted from first heating device 10 is absorbed to a smaller part by the fluid, which in a common embodiment consists of water or a solution of cooking salt, and to a larger part energy radiates out and is absorbed in the surrounding tissue. Energy is supplied via feed cable 15 from energy supply unit 41 (see FIG. 6). The electromagnetic radiation emits energy to the surrounding tissue up to a certain distance from the urethra. In a preferred embodiment first heating device 10 comprises a coil antenna.

In FIG. 1, reservoir 11 is expanded to its working volume by fluid 13 that has been conducted into it. Reservoir 11 is then the shape of a cigar with its greater length in the longitudinal direction of the treatment catheter. Reservoir 11 is arranged on the outside of the treatment catheter and in one embodiment can have a somewhat larger part of reservoir 11 on the underside of the treatment catheter. With expansion of reservoir 11 the treatment catheter is lifted upwards. Fluid 13 is conducted through channel 22 that is designed as a tube that extends through treatment catheter 12 (see also FIG. 2). During treatment a second heating device 29 heats the liquid in reservoir 11. The expansion of reservoir 11 leads to very good contact against the prostatic urethra.

By carrying out heat treatment of the prostate tissue with two independent energy sources it is possible effectively to treat different parts of the prostate. With the invention it is thus for the first time possible to treat with heat in an effective and simultaneous manner i) the base of the bladder, ii) the prostatic urethra and adjacent area along with iii) parts in the prostate located farther away.

Feed cable 15, through which first heating device 10 is supplied with energy, becomes hot as a result of cable losses.

Losses in the feed cable are typically around 1 dB per meter at the microwave frequencies that are commonly employed (500-2500 MHz). In order to avoid thermally induced injury to tissue because of these cable losses outside the area of treatment, for example on the sphincter muscle that surrounds the urethra outside the prostate, feed cable 15 is cooled. This is accomplished by cooling channels 27 that are included in treatment catheter 12 (see also FIG. 4). preferably around feed cable 15. In an embodiment according to the invention cooling channels 27 have a delimitation wall 28, at which cooling fluid circulating in cooling channels 27 returns. In this way cooling of heating device 10, reservoir 11, and the prostatic urethra with its mucous membrane is prevented. This means in turn that the power that has to be supplied from unit 14 can be decreased in comparison with techniques that use cooled treatment catheters and where cooling is done along the prostatic urethra. With lower power levels the risk of malpractice is lessened along with injury to healthy tissue outside the prostate.

In the treatment catheter fluid channel 26 that ends in balloon 18 is also present. Through it fluid can be supplied for expansion of balloon 18 when the treatment catheter is brought into the desired position for treatment. Fluid channel 26 is also used in order to empty balloon 18 after treatment is completed and before the treatment catheter is withdrawn from the urethra. A conventional hypodermic needle or similar is suitably used for the filling and emptying of balloon 18.

The heating of bladder neck 21' and an adjacent part of prostatic urethra 40 that can be brought about by first heating device 10 is in many cases insufficient, especially in the area near bladder 21. In order to increase the possibility of heating in this area a second heating device 29 is therefore arranged in treatment catheter 12 inside fluid reservoir 11. Second heating device 29 comprises in one embodiment a resistance wire or similar with good heat transfer through treatment catheter 12 and the liquid in fluid reservoir 11.

In the embodiment shown in FIG. 1, the coil antenna also embodies second heating device 29 in that the coil antenna is embodied with both inductance L, a certain capacitance, and, with suitable direct current resistance R. See also FIG. 6. The coil antenna is supplied both with microwave energy and direct current (or low frequency alternating current) and thus functions both as a microwave-emitting unit and as a resistive heating element. According to one embodiment direct current is supplied in parallel simultaneously with microwave energy from energy supply unit 14. In an alternate embodiment direct current and microwaves are supplied alternately via a coaxial relay or similar electronic component that alternately transmits microwaves and direct current, respectively, in feed cable 15.

Fluid 13 in the reservoir is heated by second heating device 29 to such a temperature that adjacent tissue is heated for example to 140° F. (60° C.) and coagulates. At this temperature the duration of treatment is about 1 hour. Depending on the size of the area to be treated and the chosen temperature of treatment the duration of treatment can be chosen to be both shorter and longer. By raising the treatment temperature in fluid reservoir 11 via second heating device 29 to a range of 194° F.-302° F. (90° C.-150° C.) the duration of treatment can be decreased to an order of some minutes, for example 5-20 minutes. At these hihg temperatures the tissue hardens and forms a shell and can at least for a transitional time function as a so-called stent.

Since the highest temperature is reached in the tissue closed to reservoir 11, the prostatic urethra, and the mucous membrane in the urethra, i.e. the part of the urethra that passes through the prostate in the area of treatment, will to a hihg degree be affected and thus destroyed. This part of the urethra reforms relatively quickly, however. Temperature sensors 23, 23', and 23" are arranged on carrier 24 in order to be able to track the temperature development during heat treatment. Carrier 24 can be extended through a channel or tube 25, which runs through the treatment catheter. Carrier 24 or temperature sensor 23 is suitably embodied with, or as, a tip that can penetrate in part a membrane or wall in the treatment catheter and in part the bodily tissue. Tube 25 is embodied so that carrier 24 with temperature sensors 23 is extended out of the treatment catheter at a suitable angle and can be driven out to a suitably radial distance from the treatment catheter. It is also possible to array several carries for the different temperature sensors 23.

A second temperature sensor 37 can also be arranged in treatment catheter 12 in or, as in the embodiment shown, inside reservoir 11 and preferably in heat-conducting contact with reservoir 11.

Heating of tissue also occurs partly at a short distance by heating of the fluid contained in the reservoir, which emits heat directly via heat conduction to adjacent tissue, and partly at a longer distance by electromagnetic radiation. The total area of treatment is larger than with conventional heating, which means that larger portions of tissue can be reached and that treatment can be adjusted better for every patient and for conditions relevant to the patient than was the case with previously known technology.

A resultant best profile, i.e. a curve which indicates the temperature of tissue radially outwards from the center of the treatment catheter, is more elongated than when only microwave or direct heat is used. It thus becomes possible to treat a larger volume. Through the fact that power from different energy sources controls both heating elements it is possibly precisely to control the appearance of the heat profile. In large prostate glands it can, for example, be advantageous to use a relatively high degree of microwave energy with a longer range, while small prostate glands can be treated with the second directly heating element with a shorter range.

First heating device 10 and second heating device 29 are preferably arranged so that the heating power can be controlled independently of each means of heating. A larger prostate is suitably treated with high power in the two hating device 10 and 29, while a smaller prostate is treated primarily or entirely with the second heating device 29. The latter course is also followed if it has been confirmed that the change in the tissues occasioned by disease is concentrated at the bladder neck and adjacent prostate tissue.

The bladder neck is most often a problem when heat treating BPH, because the bladder neck often has a high degree of blood flow and thus a high transfer away of heat. The result is that the temperature often doe not become sufficiently high to bring about a coagulation of tissue merely with microwaves. This problem is avoided with the invention as now designed in that the bladder neck is instead mainly heated directly by second heating device 29 and the liquid in fluid reservoir 11. The liquid, which is in good thermal contact with the bladder neck, has such a high temperature (>140° F.; 60° C.) that the outer parts of the bladder neck are coagulated because of heat transfer. If the temperature in fluid reservoir 11 is sufficiently high, the blood flow in the bladder neck no longer matters, since the coagulation of the tissue happens very quickly.

When treatment has ended, the supply of energy to heating device 10 and 29 is interrupted and reservoir 11 is allowed to return to normal body temperature. It is unsuitable to remove the treatment catheter as long as the reservoir has a temperature that can cause injury when the reservoir is passed through the body. For this reason the temperature in reservoir 11 is registered constantly, so that removal of the treatment catheter can occur as soon as the desired temperature has been reached.

When catheter 12 is introduced into the urethra with a tip in urinary bladder 21, drainage of urine and perhaps other liquid from the urinary bladder can occur through a drainage channel incorporated in catheter 12. The drainage channel runs through the whole length of catheter 12 and ends with an opening 20 near the tip of catheter 12. With certain types of treatment it can be suitable to leave catheter 12 for some time after treatment. Even during this time the function of the drainage channel is to drain the urinary bladder.

As soon as urine again passes through the urethra in the prostate, the treated and dead tissue will be able to flush with the urine. A remaining cavity in the prostate caused by removed tissue assures the passage of urine in the correct manner. The cavity initially has a form that corresponds with the form of reservoir 11 during the time of treatment, i.e. with the largest cross-area closest to urinary bladder 21. The healing process including the rejection of coagulated tissue can continue for a time of some months.

As a complement to, or part of, the heat treatment according to the above, some form of medicine can be introduced into fluid reservoir 11 Fluid reservoir 11 is modified in that case so that is allows passage of the medicine. Fluid reservoir 11 is suitably embodied so that the medicine can diffuse through the wall of fluid reservoir 11, but it is also possible to incorporate permeable channels or similar in the wall. According to one treatment, medicine against pain can be included in the fluid. Other medicines can also be used for direct treatment.

Figure 2:
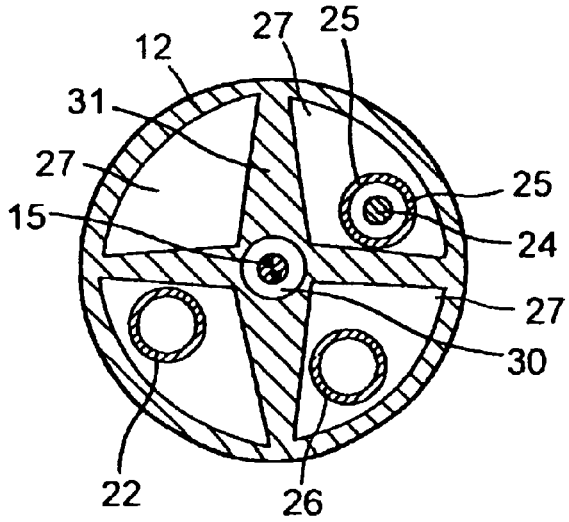
FIG. 2 is a transverse sectional view from line II-II in FIG. 1.

FIG. 2 schematically shows an embodiment of a treatment catheter 12. Treatment catheter 12 is designed with a number of cavities and channels extending along the treatment catheter. Feed cable 15 runs through a central cavity 30, which is preferably well shielded. Cooling fluid is transported in separated cooling channels 27, preferably in a circulating system. In a first cooling channel 27 a tube 25 for carrier 24 is arranged. In a similar manner fluid channel 26 for balloon 18 and channel 22 for fluid reservoir 11 are arranged in other channels 27. A drainage channel, which ends in opening 20 in the treatment catheter, can be arranged in a similar way in a cooling channel.

Figure 3:
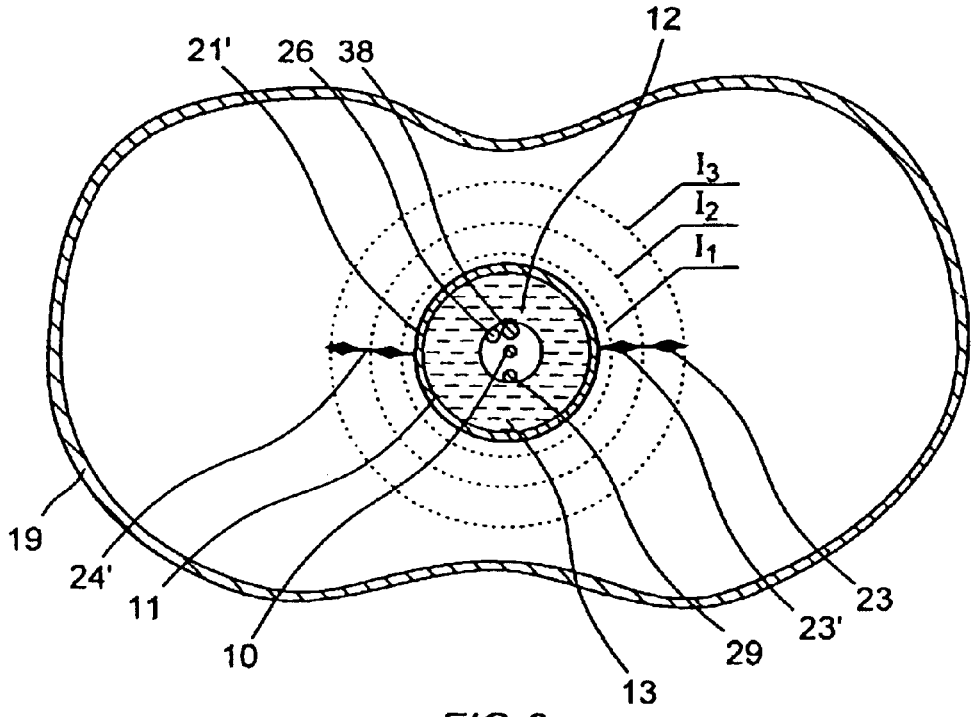
FIG. 3 is a transverse cut through the prostate along line III-III in FIG. 1 and a treatment catheter inserted into it.

In FIG. 3 is shown schematically in cross section how the propagation of heat primarily from second heating device 29 extends through prostate 19 with an ever lower intensity. Intensity $I_1$ is closest to fluid reservoir 11. The intensity drops off quickly to level $I_2$ and sinks to level $I_3$ at a farther distance from fluid reservoir 11. In the area closest to fluid reservoir 11 the temperature of the tissue can be raised to a very high level as a result of the high intensity level $I_1$ so that the tissue hardens into a shell, especially as adjacent prostate tissue is compressed to a certain degree. The compressed prostate tissue also leads to a lessened need for power, since less heat is transferred by blood flow.

Figure 4:
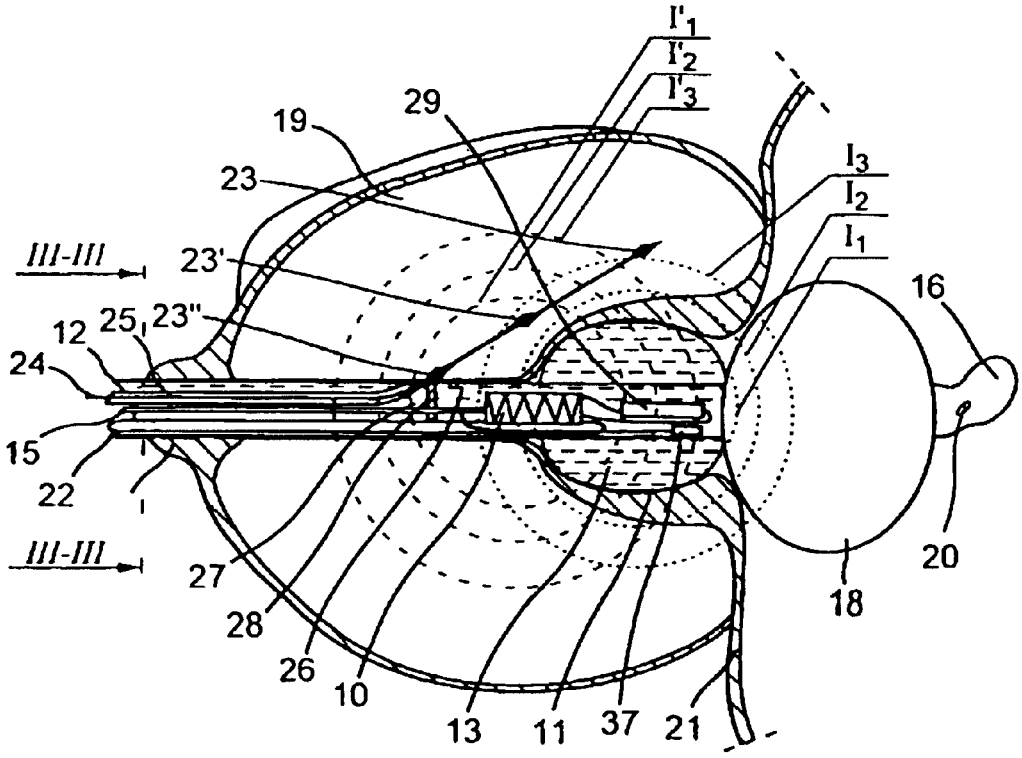
FIG. 4 is a principal cross-sectional view in the longitudinal direction of an alternate embodiment of a treatment catheter according to the invention.

In the embodiment according to FIG. 4, fluid reservoir 11 has a shorter extension in the longitudinal direction of the treatment catheter and assumes its active position completely within the upper part of the urethra closest to bladder neck 21'. This design is especially usable when the area that should be primarily treated lies around the bladder neck. First heating device 10 is suitably activated so that treatment with microwave-induced heat is concentrated in the area around the central prostate. The second heating means assures that the area closest to the balloon and especially bladder neck 21' receives effective treatment. Second heating device 29 according to this embodiment makes possible higher treatment temperature and a more limited volume. As can be seen in FIG. 4 the radial range for heat propagation is greater for the radiating microwave component than for the directly applied component from reservoir 11, where heat is transported out of the tissue through heat conduction. Intensity levels $I'_1$, $I'_2$, $I'_3$ which are produced by first heating device 10 are located at a farther distance from treatment catheter 12 than corresponding intensity levels from second heating device 29.

In the embodiment shown in FIG. 4, first heating means 10 consists of coil antenna with low or negligible resistive power loss. Second heating means 29 includes instead a resistive heating element, for example, in the form of a resistance wire or a resistor (see also FIG. 7).

Figure 5:
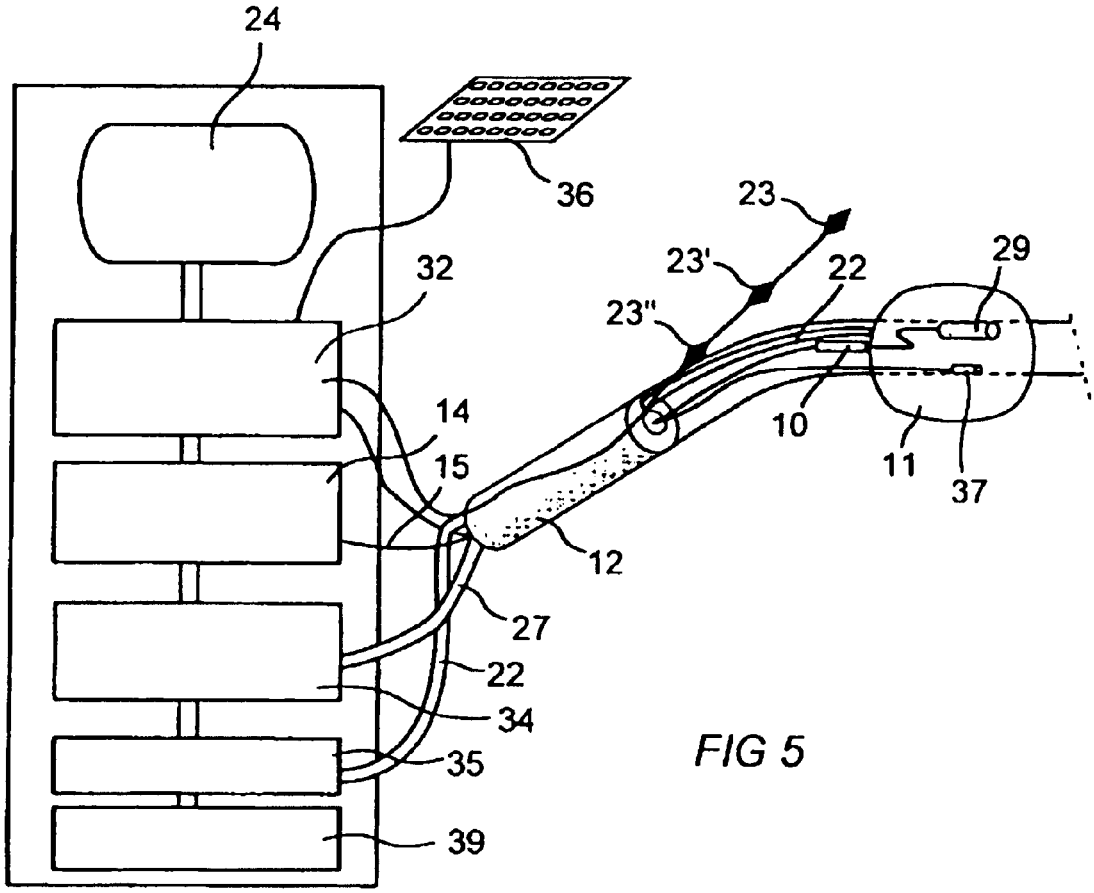
FIG. 5 is a principal block diagram that shows how a treatment catheter can be included in a treatment assembly.

The block diagram in FIG. 5 schematically shows the various function blocks that can be included in a treatment assembly with a treatment catheter according to the invention. As indicated above, energy is supplied to heating device 10 from energy supply unit 14. A central control unit 32 is operatively connected with energy supply unit 14 and a display unit 33 and with a pumping and cooling device 34 and a fluid supply device 35. Control unit 32 is additionally operatively connected with an input device, for example, in form of a keyboard 36. Control unit 32, keyboard 36, and display unit 33 can also be included in a conventional computer with a monitor and keyboard.

Control unit 32 is operatively connected with temperature sensor 23 and 37 and can control energy supply unit 14 dependent on the current temperature in the area of treatment so that suitable power is supplied to heating device 10. In this manner it is possible to increase the temperature considerably with good safety in fluid reservoir 11 and thus in surrounding tissue so that tissue death occurs in the desired way. Data on temperature from temperature sensors 23 and 37 can also be shown continuously on display unit 33.

Pumping and cooling device 34 is connected with cooling channels 27 and pumps suitable cooling fluid through cooling channels 27 in order primarily to cool feed cable 15 while it is being extended forward to heating device 10. Fluid supply device 35 is used when fluid reservoir 11 is to be filled and expanded. The filling can be monitor ed by control unit 32.

A preferred embodiment according to the invention also includes a pressure meter 39, which is operatively connected with fluid supply device 35. Pressure meter 39 is also operatively connected with central control unit 32 in order that the pressure in fluid reservoir 11 can influence the process of treatment. The pressure can be changed depending on now the treatment is progressing. For reasons of safety the treatment should be able to be interrupted if the pressure in fluid reservoir 11 falls abruptly, for example, for the reason that fluid reservoir 11 breaks.

Reservoir 11 is completely closed and contains a certain volume of fluid 13 with suitable properties of heat transfer. Examples of such fluids are silicon oil and water. Reservoir 11 is embodied of elastic silicon or another material with corresponding elastic properties, for example, latex. Even treatment catheter 12 can be embodied of silicon or similar material, as can bladder 18.

Figure 6:
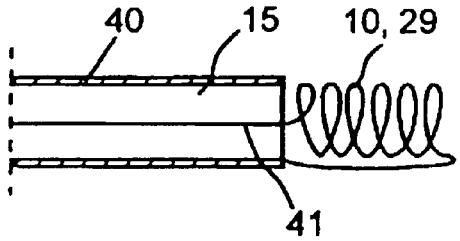
FIG. 6 shows a primary principal embodiment of a combined heating device included in the invention.

The embodiment shown in FIG. 6 includes feed cable 15 in form of a coaxial cable with shielding covering 40 and inner conductor 41. The covering also constitutes an outer conductor. At the end of covering 40 the inner conductor is then an antenna, which in this embodiment is a coil-wound antenna. Other embodiments of the antenna are also possible within the framework of the invention.

First heating device 10 and second heating device 20 are comprised of a combined means in the form of the coaxial cable that conducts microwaves to a radiator (antenna) and direct current or low-frequency alternating current to a resistor. The resistor and the radiator are comprised of the same physical construction, which functions differently dependent on whether it is fed with microwaves or direct current/low-frequency alternating current. In this variant the antenna itself is comprised of a closed loop with a certain inductance L and a resistance R that connects the inner conductor of the coaxial cable with the outer conductor in such a way that the loop, when it is fed with microwave energy, functions as an antenna and radiates the energy. In the case when it is fed with direct current/low frequency alternating current it functions only as a resistive load and develops heat when the current passes through the loop. The antenna also displays a certain capacitance.

In a typical case the loop has a pure resistance in the range of 1-20 ohms, for example 1 ohm with direct current, while with high frequency (HF) it has 50 ohms as a result of inductance of the coil. The resistive load will be a lesser part of the total HF-load, so that the larger part of supplied microwave power radiates out from the antenna. The material in the coil is chosen so that suitable resistance is obtained (i.e., in th range of some ohms). When such an antenna is fed with 40 watt microwave power (a typical value with microwave treatment), in the above-mentioned case 1/50*40=0.8 watt heating power will be developed in the radiator itself, while 49 watts radiate out. This means that the antenna does not significantly affect the temperature of the fluid in reservoir 11 through direct effect, since 0.8 W is too little power to cause effective heating of reservoir 11.

Conversely, when the construction is used instead only with direct current/low frequency alternating current 25W of heat will be developed and directly heat the fluid in balloon 11 at an input current of 5 amperes (5 volts input). It is worth nothing that the coaxial cable is a suitable carrier of both microwave energy and direct current/alternating current up to some tens of amperes. By using coaxial cable 15 in this dual manner, one gains the advantage of having a cable system that at the same time is tough enough to conduct both microwave energy and high current (10A) at a low voltage (for example 10 Volts). This means that one can aviod high voltage for the direct current component with its concurrent safety risk for the patient.

Figure 7:
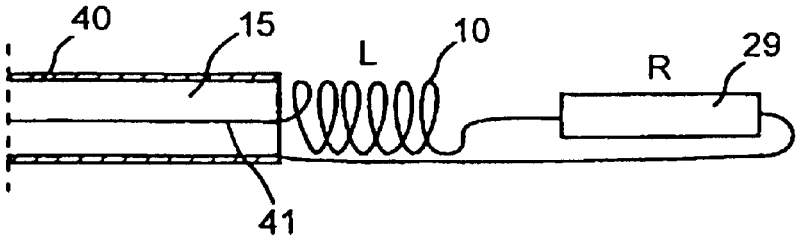
FIG. 7 shows another principal embodiment of two heating devices included in the invention and FIG. 8 is a principal block diagram that shows how energy can be supplied to two heating devices included in the invention.

In an alternate embodiment according to FIG. 7 first heating device 10 is physically separated from second heating device 29. The radiating element that constitutes first heating device 10 includes a low-resistive loop (coil). The coil is connected in series with resistance arranged inside fluid reservoir 11, typically in the range of some few ohms, for example, 5 ohms. The resistance in a preferred embodiment is placed far forward closest to bladder neck 21' and the microwave radiator is located farther back and centrally in the prostate. With this embodiment it is possible to achieve effective heating of an arbitrary part of the prostatic urethra with its mucous membrane and of the tissue located near it through suitable positioning of fluid reservoir 11. This embodiment is especially suitable when the tissue surrounding the prostatic urethra closest to bladder neck 21' and bladder neck 21' itself are to be treated. At the same time central parts of prostate 19 can be treated in a conventional manner with microwave radiation from first heating device 10.

Figure 8:
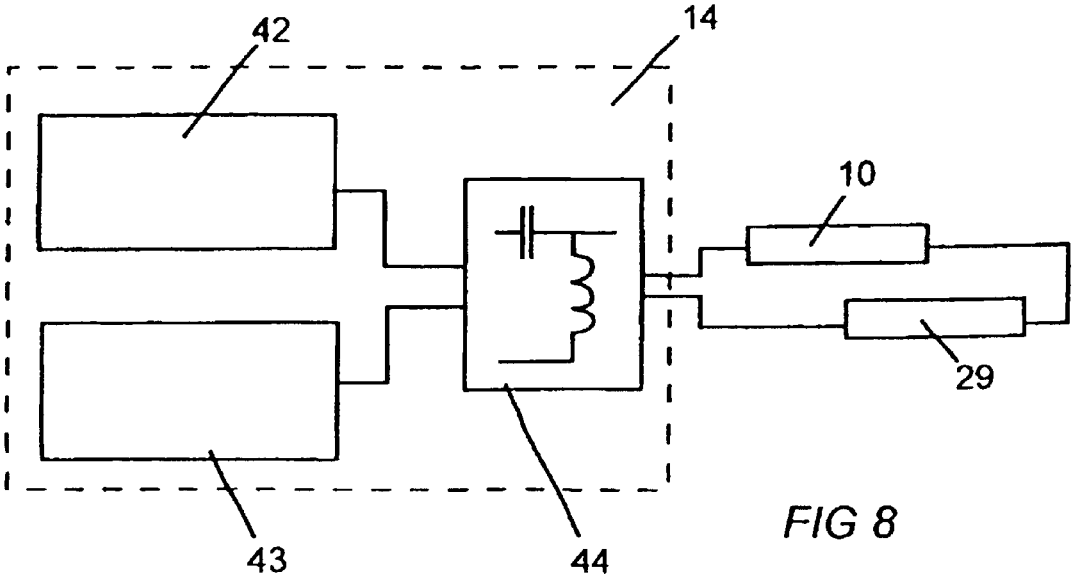

FIG. 8 generally shows components that can be included in energy supply unit 14. A microwave generator 42 produces microwave energy at a suitable frequency and a DC assembly 43 produces direct current. Microwave generator 42 and DC assembly 43 are both connected with an electronic unit 44, which in an embodiment according to the invention alternately supplies direct current and microwave energy to heating device 10, 29. Electronic unit 44 can include a coaxial relay that alternatively transmits direct current/low frequency alternating current in feed cable 15 and alternating micowaves.

By alternately transmitting microwaves and direct current/low feruqncy alternating current through the construction, the operator has the possibility to moderate the temperature in fluid reservoir 11 with the resistive part of the invention in order to achieve coagulation of tissue in close proximity to the prostatic urethra including the bladder neck. The temperature in fluid reservoir 11 should not be less than 140 (60° C.) and best up towards 176° F.-194° F. (80° C.-90° C.) or more. This is in order to make brief treatment possible. During the microwave phase more peripherally lying areas are affected, but the temperature there will be lower, around 122° F.-140° F. (50° C.-60° C.). For this reason the time taken in order to achieve coagulation of tissue in these more distant areas will be correspondingly longer. The microwave part is especially important for larger prostate glands because of its greater range in comparison with pure heat conduction. Typical radial penetration of coagulation by means of heat conduction from fluid reservoir 11 is 5-8 mm. Corresponding penetration of coagulation by microwaves is up to 20-30 mm.

In a typical embodiment the system is run in multiplex intervals of 1-60 seconds with microwaves and 1-60 seconds with direct current/low feruqncy alternating current depending on which temperature obtains at the time in peripheral area of the prostate or in the area near the prostatic urethra, after which the sequence is repeated. In an alternate embodiment the treatment is first completed with the fluid typically for 15 minutes without interruption, and after that using only microwaves for another 45 minutes.

In an alternate embodiment in accordance with the invention electronic unit 44 includes a so-called bias-tee component. This isolates microwave generator 42 from direct current assembly 43, so that these are simultaneously connected with feed cable 15. In this way microwave energy can be supplied at the same time as direct current or low frequency current. The different characteristics dependent on frequency in first heating device and second heating device 29 mean that microwave energy or direct current energy can be supplied and emitted simultaneously from the respective heating devices. A bias-tee component includes, as in indicated in FIG. 8, essentially a condenser for isolation of microwave generator 42 from direct current assembly 43 and an inductance for isolation of direct current assembly 43 from microwave generator 42.

What is claimed is:

1. A device for heat treatment of the prostate *of a patient*, comprising a treatment catheter with an expandable fluid reservoir containing liquid and first heating means which is located within said treatment catheter and *which* emits electromagnetic radiation for heating of the surrounding prostatic tissue, said treatment catheter being provided with a free end which is insertable through *the* urethra into the urinary bladder of [a] *the* patient and a second end connected to an energy supply unit arranged outside of the patient's body, wherein second independent heating means is provided in thermal contact with the liquid in the fluid reservoir for heating of the liquid in the fluid reservoir;

said fluid reservoir is positioned external to the treatment catheter so that in its operative position it engages with and fills *the* urethra which extends through *the* prostate adjacent to the [prostate] *bladder* neck *of the patient*, and said first heating means and second heating means are operatively connected with the energy supply unit, wherein said first heating means is provided as a coil antenna and said second heating means comprises a lead resistance in said coil antenna.

2. A device according to claim 1, wherein said first heating means is provided as an antenna element emitting microwaves and said second heating means *also* comprises an electric lead resistance *connected to said antenna element*.

3. A device according to claim 2, wherein said second heating means comprises a lead resistance separated from the antenna element and provided axially displaced along the treatment catheter from said first heating means towards the free end of the treatment catheter.

4. A device according to claim 1, wherein said energy supply unit comprises a microwave generator for supply of microwave energy to said first heating means and *one of* a direct current or *a* low frequency power source for supply of electric energy to said second heating means.

5. A device according to claim 4, wherein said first heating means is electrically connected to said second heating means and the microwave generator is operatively connected to said *one of the direct current or the* low frequency power source for jointly supplying microwave energy and electric energy to said first heating means and said second heating means.

6. A device according to claim 4, wherein a first temperature sensor is provided for measuring of temperature in the prostatic tissue and a second temperature sensor is provided for measuring of temperature in the fluid reservoir, and wherein a central control unit operatively connected to said energy supply unit is provided for controlling the supply of microwave energy to said first heating means as a function of the temperature in the prostatic tissue and for controlling the supply of electric energy to said second heating means as a function of the temperature in the fluid reservoir.

7. A device according to claim 1, wherein said energy supply unit is connected to said first heating means and to said second heating means via an electronic unit, and wherein said electronic unit is provided for simultaneous supply of energy to the two heating means.

8. A device according to claim 1, wherein said energy supply unit is connected to said first heating means and to said second heating means via an electronic unit, and wherein said electronic unit is provided for non-simultaneous supply of energy to the two heating means.

9. A device for heat treatment of the prostate *of a patient*, comprising a treatment catheter with an expandable fluid reservoir *containing liquid* and first heating means which is located within said treatment catheter and *which* emits electromagnetic radiation for heating of the surrounding prostatic tissue, said treatment catheter being provided with a free end which is insertable through *the* urethra into the urinary bladder of [a] *the* patient and a second end connected to an energy supply unit arranged outside of the patient's body, wherein second independent heating means is provided in thermal contact with the liquid in the fluid reservoir for heating of the liquid in the fluid reservoir, said fluid reservoir is positioned external to the treatment catheter so that in its operative position it engages with and fills *the* urethra which extends through *the* prostate adjacent to the [prostate] *bladder* neck *of the patient*, and said first heating means and second heating means are operatively connected with the energy supply unit;

said first heating means is provided as an antenna element emitting microwaves and said second heating means comprises an electric lead resistance; and wherein a feed cable connects said energy supply unit to said first heating means and to said second heating means, and wherein said feed cable is provided as a coaxial cable with an inner conductor for supply of microwave energy and electric energy and with a covering acting as a return lead.

10. A method according to claim [9]*14*, comprising [supply of] *supplying* microwave energy to said first heating means simultaneously with [supply of] *supplying* electric energy to said second heating means.

11. A method according to claim 10, comprising

[continual] *continually* measuring of the temperature of the prostatic tissue and the liquid in the fluid reservoir, and

[control of] *controlling* the supply of microwave energy as a function of the temperature of the prostatic tissue, and [control of] *controlling* the supply of electric energy as a function of the temperature of the liquid in the fluid reservoir.

12. A method according to claim [9]*14*, comprising [supply of] *supplying* microwave energy to said first heating means non-concurrently with [supply of] *supplying* electric energy to said second heating means.

13. A device for heat treatment of the prostate *of a patient*, comprising a treatment catheter with an expandable fluid reservoir *containing liquid* and first heating means which is located within said treatment catheter and *which* emits electromagnetic radiation for heating of the surrounding prostatic tissue, said treatment catheter being provided with a free end which is insertable through *the* urethra into the urinary bladder of [a] *the* patient and a second end connected to an energy supply unit arranged outside of the patient's body, wherein second independent heating means is provided in thermal contact with the liquid in the fluid reservoir for heating of the liquid in the fluid reservoir, said fluid reservoir is positioned external to the treatment catheter so that in its operative position it engages with and fills *the* urethra which extends through *the* prostate adjacent to the [prostate] *bladder* neck *of the patient*, and said first heating means and second heating means are operatively connected with the energy supply unit, wherein a feed cable connects said energy supply unit to said first heating means and to said second heating means, and wherein said feed cable is provided as a coaxial cable with an inner conductor for supply of microwave energy and electric energy and with a covering acting as a return lead.

14. A method for heat treatment of the prostate *of a patient*, comprising *using* a treatment catheter equipped with an expandable fluid reservoir and first heating means which is located within said treatment catheter and *which* emits electromagnetic radiation for heating of the prostatic urethra as well as the prostatic tissue surrounding the urethra *of the patient*, wherein said treatment catheter is provided with a free end which is inserted through *the* urethra into the urinary bladder of [a] *the* patient, and a second end *which* is connected to an energy supply unit arranged *and used* outside of the patient's body, comprising the following steps:

[operative connection of] *operatively connecting* said first heating means to the energy supply unit, positioning [of] said fluid reservoir externally to the treatment catheter so that in its operative position it will expand and engage with *the* urethra which extends through *the* prostate adjacent to the [prostate] *bladder* neck *of the patient*, [and]

heating [of] liquid in the fluid reservoir through second heating means which is arranged to be in thermal contact with the liquid separately from said first heating means, [wherein said method comprising]

heating [of] deep-lying prostatic tissue through emitting of microwave energy from said first heating means, and

[destruction of] *destructing* the prostatic urethra, its mucousa and the closest surrounding tissue as well as the bladder [base] *neck* primarily via direct heating *from the liquid* through said second heating means.

*15. A method according to claim 14, further comprising:*

*arranging the second heating means in thermal contact with the liquid by positioning the second heating means within the fluid reservoir.*

*16. A method according to claim 14, further comprising:*

*heat treating the deep-lying prostate tissue outward beyond that tissue destructed by heat conduction from the fluid reservoir by emitting electromagnetic radiation.*

*17. A method according to claim 14, further comprising:*

*expanding the fluid reservoir in radial size relative to adjoining portions of the treatment catheter during the heat treatment of the prostate.*

*18. A method according to claim 17, further comprising:*

*pressurizing the liquid within the fluid reservoir to expand the fluid reservoir in radial size during the heat treatment of the prostate.*

*19. A method according to claim 17, further comprising:*

*compressing the surrounding tissue to reduce blood flow through the compressed tissue to reduce the transmission of heat by blood flow away from the compressed tissue.*

*20. A method according to claim 17, further comprising:*

*compressing the bladder neck to reduce blood flow through the bladder neck to reduce the transmission of heat by blood flow away from the compressed bladder neck.*

*21. A method according to claim 17, further comprising:*

*destructing the prostatic urethra, its mucosa and the closest surrounding prostate tissue as well as the bladder neck by coagulation primarily from heat conducted from the heated liquid in the fluid reservoir; and*

*destructing the deep-lying prostate tissue outside of the closest surrounding prostate tissue by heat from emitted electromagnetic radiation.*

*22. A method according to claim 17, further comprising:*

*creating a shell of tissue of larger transverse dimensions than the transverse dimension of the prostatic urethra prior to the heat treatment.*

*23. A method according to claim 17, further comprising:*

*creating a stent of tissue through the prostate by the heat treatment.*

*24. A method according to claim 17, further comprising:*

*creating a cavity by the destructed tissue, the cavity having larger transverse dimensions than the transverse dimension of the prostatic urethra prior to the heat treatment.*

*25. A method according to claim 14, further comprising:*

*transmitting heat to the liquid in the fluid reservoir from both the first and second heating means.*

*26. A method according to claim 14, further comprising:*

*transmitting heat to the liquid in the fluid reservoir from electromagnetic radiation emitted from the first heating means and transmitting heat to the liquid in the fluid reservoir from heat conduction from the second heating means.*

*27. A method according to claim 26, wherein the first heating means comprises an antenna element for emitting the electromagnetic radiation, and said method further comprises:*

*transmitting heat to liquid in the fluid reservoir by heat conduction from the antenna element when the antenna element emits electromagnetic radiation.*

*28. A method according to claim 14, wherein the catheter comprises a feed cable extending from the second end to the first heating means, and the first heating means comprises an antenna element emitting electromagnetic radiation, and said method further comprises:*

*conducting energy from the energy supply unit through the feed cable to the antenna element to cause the antenna element to emit the electromagnetic radiation; and*

*cooling the feed cable by conducting liquid along the feed cable to transfer heat from the feed cable caused by conducting the energy to the antenna element.*

*29. A method according to claim 28, further comprising:*

*preventing damage to the urethra at locations adjacent to the feed cable and outside of the fluid reservoir by cooling the feed cable by conducting the liquid along the feed cable.*

*30. A method according to claim 14, further comprising:*

*simultaneously supplying energy to the first and second heating means to heat the liquid within the fluid reservoir.*

*31. A method according to claim 14, further comprising:*

*measuring temperature of the prostatic tissue,*

*measuring of temperature of liquid in the fluid reservoir,*

*controlling the supply of electromagnetic energy to said first heating means as a function of the temperature in the prostatic tissue, and*

*controlling the supply of electric energy to said second heating means as a function of the temperature of the liquid in the fluid reservoir.*

*32. A method according to claim 14, further comprising:*

*closing the fluid reservoir to contain the liquid within the fluid reservoir.*

*33. A method according to claim 14, further comprising:*

*conducting liquid into and out of the fluid reservoir through a channel which extends from the free end of the treatment catheter into the fluid reservoir.*

*34. A method according to claim 14, wherein the treatment catheter further comprises an expandable balloon, and the method further comprises:*

*expanding the expandable balloon with the urinary bladder; and*

*contacting the expandable balloon with the bladder neck to position the treatment catheter in a treatment position in the urethra at which heat from the liquid in the fluid reservoir is transferred directly to the bladder neck.*

*35. A method according to claim 14 comprising heating the liquid in the reservoir to a temperature of at least 60 degrees Celsius.*

*36. A method according to claim 14 comprising diffusing medicine from the fluid reservoir to the adjacent exterior tissue contacted by the fluid reservoir.*

*37. A device according to claim 1 wherein the coil antenna and the lead resistance conduct heat into the liquid within the fluid reservoir.*

*38. A device according to claim 1 further comprising a feed cable extending within the treatment catheter from the second end to the first heating means to conduct microwave energy to the first heating means, and a cooling channel located adjacent to the feed cable and extending within the treatment catheter from the second end to a location adjacent to the fluid reservoir.*

*39. A device according to claim 38 wherein liquid in the cooling channel transfers heat from the feed cable resulting from the conduction of microwave energy to the first heating means.*

*40. A device according to claim 2 wherein said electrical lead resistance is also located within the fluid reservoir.*

*41. A device according to claim 9 wherein the electric lead resistance is in the antenna element.*

*42. A device according to claim 13 wherein said first heating means comprises an antenna element emitting microwaves.*

*43. A device according to claim 9 or 42 wherein said antenna element comprises a coil.*

*44. A device according to claim 9 or 13 wherein said second heating means comprises an electrical resistance.*

*45. A device according to claim 44 wherein the electrical resistance is in the antenna element.*

*46. A device according to claim 9 or 13, wherein said energy supply unit comprises a microwave generator for supplying microwave energy to said first heating means and one of a direct current or a low frequency power source for supplying electric energy to said second heating means.*

*47. A device according to claim 46, further comprising:*

*a first temperature sensor for measuring of temperature of the prostatic tissue;*

*a second temperature sensor for measuring of temperature of liquid in the fluid reservoir; and*

*a central control unit operatively connected to said energy supply unit for controlling the microwave energy supplied to said first heating means as a function of the temperature in the prostatic tissue and for controlling the electric energy supplied to said second heating means as a function of the temperature of the liquid in the fluid reservoir.*

*48. A device according to claim 9 or 13 wherein the feed cable extends within the treatment catheter from the second end to the first and second heating means by which to conduct the microwave energy to the first heating means and the electrical energy to the second heating means, and the treatment catheter further comprises a cooling channel located adjacent to the feed cable and extending within the treatment catheter from the second end to a location adjacent to the fluid reservoir.*

*49. A device according to claim 48 wherein liquid in the cooling channel transfers heat from the feed cable resulting from the conduction of microwave energy to the first heating means.*

*50. A device according to claim 1, 9 or 13, wherein the operative position of the fluid reservoir is an expansion in radial size of the fluid reservoir relative to adjoining portions of the treatment catheter.*

*51. A device according to claim 50, wherein the expansion in size results from pressurizing the liquid within the fluid reservoir.*

*52. A device according to claim 50, wherein the expansion in radial size of the fluid reservoir is sufficient to compress the surrounding tissue to reduce blood flow through the compressed tissue and thereby reduce the transmission of heat by blood flow away from the compressed tissue.*

*53. A device according to claim 52, wherein the surrounding tissue which is compressed to reduce blood flow includes the bladder neck.*

*54. A device according to claim 52, wherein the surrounding tissue which is compressed to reduce blood flow includes the prostate tissue surrounding the prostatic urethra adjacent to the bladder neck.*

*55. A device according to claim 1, 9 or 13, wherein the fluid reservoir is closed to contain the liquid within the fluid reservoir.*

*56. A device according to claim 1, 9 or 13, wherein the treatment catheter further comprises a balloon which is expandable within the urinary bladder to position the treatment catheter in a treatment position in the urethra at which heat from the liquid in the fluid reservoir is transferred directly to the bladder neck.*

*57. A device according to claim 56, wherein the first heating means is located in the treatment catheter to emit radiation to heat prostate tissue when the treatment catheter is in the treatment position.*

*58. A device according to claim 1, 9 or 13, wherein said energy supply unit supplies energy to the first heating means separately from energy supplied to the second heating means.*

*59. A device according to claim 1, 9 or 13, wherein the treatment catheter comprises a channel extending from the fluid reservoir to the second end of the treatment catheter by which to conduct the liquid into and out of the fluid reservoir.*

*60. A device according to claim 1, 9 or 13, wherein the first and second heating means have the capacity to heat the liquid in the reservoir to a temperature of at least 60 degrees Celsius.*

*61. A device according to claim 1, 9 or 13, wherein the first heating means has the capacity to treat tissue by heat created from emitted electromagnetic radiation at a greater distance from the treatment catheter than the heated liquid in the fluid reservoir has the capacity to treat tissue by heat conducted from the liquid in the fluid reservoir.*

*62. A device according to claim 1, 9 or 13, wherein the fluid reservoir is defined by an exterior wall, and the exterior wall permits diffusion of medicine within the liquid within the fluid reservoir through the wall to the exterior tissue.*

*63. A catheter for insertion into a urethra to perform a therapeutic heat treatment of a prostate which surrounds a prostatic urethra to enlarge a urine drainage passage through the prostate from a urinary bladder into a urethra of a human being, comprising:*

*an antenna located at a position within the catheter adjacent to the prostatic urethra and the prostate upon insertion of the catheter into the urethra to a treatment position at which the treatment is performed, the antenna for emitting electromagnetic radiation into the prostate to heat therapeutically with the emitted radiation a portion of the prostate surrounding a portion of the prostatic urethra;*

*an expandable reservoir within the catheter surrounding the antenna and located to extend along a portion of the prostatic urethra upon positioning the catheter in the treatment position, the reservoir for containing liquid and expanding in radial size relative to adjoining portion of the catheter upon pressuring the liquid within the reservoir, the extent of radial expansion of the reservoir being sufficient to compress tissue adjacent to the reservoir and reduce blood flow through the compressed tissue to reduce the transmission of heat by blood flow away from the compressed tissue;*

*the expandable reservoir confining the liquid to absorb heat from the antenna and from a portion of the electromagnetic radiation emitted from the antenna, the reservoir having a capacity for conductively transmitting sufficient heat from the liquid to heat therapeutically a first region of tissue immediately adjoining the expanded reservoir, the reservoir and the liquid having a capacity for transmitting sufficient electromagnetic radiation emitted from the antenna to heat therapeutically a second region of tissue located beyond the first region from the reservoir, the capacity for therapeutically heating the first and second tissue regions being sufficient to enlarge the urine drainage passage;*

*a channel extending within the catheter from a position at an exterior of the urethra and communicating with the expandable reservoir for conducting pressurized liquid into the reservoir.*

*64. A catheter as defined in claim 63, wherein:*

*the heat capacity of the expanded reservoir and the conductive transmission of heat from the liquid with the reservoir establishes the extent of the first region of therapeutically heated tissue.*

*65. A catheter as defined in claim 63, also used to therapeutically heat treat a bladder neck which surrounds the prostatic urethra extending from the urinary bladder to increase the size of the urine drainage passage, wherein:*

*the expandable reservoir is located to directly contact the bladder neck when the catheter is in the treatment position; and*

*the reservoir has a capacity for conductively transmitting sufficient heat from the liquid to heat the bladder neck therapeutically and cause an enlargement of the bladder neck for the urine passageway.*

*66. A catheter as defined in claim 63, further comprising:*

*a feed cable extending within the catheter from a position at the exterior of the urethra and connecting to the antenna to conduct energy to the antenna, the feed cable emitting heat as a result of conducting the energy to the antenna; and*

*a cooling channel within the catheter and extending along the feed cable, the cooling channel for conducting liquid to remove heat emitted by the feed cable and to protect the urethra and the tissue surrounding the feed cable from heat from the feed cable when the catheter is in the treatment position.*

*67. A catheter as defined in claim 66, wherein:*

*the cooling channel extending along the feed cable and the channel communicating with the expandable reservoir are separate from one another.*

*68. A catheter as defined in claim 66, wherein:*

*the expandable reservoir is separated from the cooling channel.*

*69. A catheter as defined in claim 66, wherein:*

*the expandable reservoir prevents circulation of the liquid in the reservoir.*

*70. A catheter as defined in claim 63, further comprising:*

*a liquid temperature sensor positioned within the reservoir to sense the temperature of liquid within the reservoir.*

*71. A catheter as defined in claim 63, further comprising:*

*a tissue temperature sensor connected to the catheter to sense the temperature of the tissue surrounding the reservoir.*

*72. A catheter as defined in claim 71, further comprising:*

*a carrier moveably positioned within the catheter, the carrier having a tip which penetrates into the prostate at a radial distance relative to the expandable reservoir upon extension of the carrier from the catheter when the catheter is in the treatment position; and wherein;*

*the tissue temperature sensor is connected to the carrier at a position which measures the temperature of the prostate at distance away from the expandable reservoir.*

*73. A catheter as defined in claim 72, wherein:*

*the tissue temperature sensor is connected to the carrier at a position which measures the temperature of the second tissue region.*

*74. A catheter as defined in claim 72, wherein:*

*the carrier includes a plurality of the temperature sensors connected at positions which measure the temperature of the prostate at a plurality of different distances away from the expandable reservoir.*

*75. A catheter as defined in claim 63, further comprising:*

*a source of additional heat for the liquid within the expandable reservoir beyond the heat from the antenna and from the emitted electromagnetic radiation.*

*76. A catheter as defined in claim 75, wherein:*

*the additional heat source is located within the expandable reservoir.*

*77. A catheter as defined in claim 75, wherein:*

*the additional heat source comprises an electrical resistance separate from the antenna.*

*78. A catheter as defined in claim 77, further comprising:*

*a feed cable extending within the catheter from a position at the exterior of the urethra and connecting to the antenna and to the electrical resistance to conduct energy to the antenna and to the electrical resistance.*

*79. A catheter as defined in claim 78, wherein:*

*the feed cable emits heat as a result of conducting the energy to the antenna; and further comprising:*

*a cooling channel within the catheter and extending along the feed cable, the cooling channel for conducting liquid to remove heat emitted by the feed cable and to protect the urethra and the tissue surrounding the feed cable from heat from the feed cable when the catheter is in the treatment position.*

*80. A catheter as defined in claim 63, in combination with an energy supply unit, the energy supply unit comprising:*

*a microwave generator for generating electromagnetic energy and electrically connected to the antenna at a position exterior of the urethra; and*

*a liquid supply device connected to the channel at a position exterior of the urethra to supply liquid through the channel to fill the reservoir with liquid and to pressurize the liquid within the reservoir to expand the reservoir; and wherein:*

*the antenna emits electromagnetic radiation from the application of the electromagnetic energy generated by the microwave generator and generates heat in the liquid in the reservoir as a result of emitting the electromagnetic radiation.*

*81. A combination as defined in claim 80, further comprising:*

*a source of additional heat for the liquid within the expandable reservoir beyond the heat from the antenna and from the emitted electromagnetic radiation; and*

*the energy supply unit further comprises a source of energy for the second heat source.*

*82. A combination as defined in claim 81, wherein:*

*the additional heat source is located in the expandable reservoir and generates heat in response to the application of electrical energy to the additional heat source; and*

*the energy supply unit further comprises an electrical energy generator connected to the additional heat source to supply electrical energy to the additional heat source.*

*83. A combination as defined in claim 82, wherein the catheter further comprises:*

*a feed cable connected to the microwave generator and the electrical energy generator, the feed cable extending from a position exterior of the urethra within the catheter and connecting to the antenna and the additional heat source to conduct microwave energy to the antenna and to conduct the electrical energy to the additional source, the feed cable emitting heat as a result of conducting the microwave energy to the antenna; and*

*a cooling channel within the catheter and extending along the feed cable; and wherein the energy supply unit further comprises:*

*a source of liquid connected to the cooling channel for conducting liquid through the cooling channel to remove heat from the feed cable and protect the urethra and the tissue surrounding the feed cable from heat from the feed cable when the catheter is in the treatment position.*

*84. A method of performing a therapeutic heat treatment of a prostate which surrounds a prostatic urethra to enlarge a urine drainage passage through the prostate from a urinary bladder into a urethra of a human being, comprising:*

*inserting into the urethra a catheter having an electromagnetic radiation emitting antenna surrounded by an expandable reservoir;*

*positioning the catheter in the urethra in a treatment position were the antenna and the reservoir are adjacent to the prostatic urethra and the prostate which are to be therapeutically heat treated;*

*filling the expandable reservoir with liquid;*

*expanding the expandable reservoir in radial size relative to adjoining portions of the catheter by pressurizing the liquid within the reservoir;*

*expanding the expandable reservoir sufficiently to compress tissue adjacent to the reservoir and reduce blood flow through the compressed tissue to reduce the transmission of heat by blood flow away from the compressed tissue;*

*energizing the antenna to emit electromagnetic radiation;*

*absorbing heat within the liquid in the reservoir from the antenna and from a portion of the electromagnetic radiation emitted from the antenna;*

*increasing the temperature of the liquid in the reservoir to a therapeutic level;*

*applying heat from the liquid within the reservoir to a portion of the prostatic urethra and a portion of the prostate surrounding the prostatic urethra;*

*conducting sufficient heat from the liquid to heat therapeutically a first region of tissue immediately adjoining the expanded reservoir, the first region including the portion of the prostatic urethra and the prostate immediately surrounding the portion of the prostatic urethra;*

*emitting sufficient electromagnetic radiation from the antenna to heat therapeutically in a second region of tissue located beyond the first region from the reservoir; and*

*enlarging the urine drainage passage by therapeutically heating the first and second tissue regions.*

*85. A method as defined in claim 84, further comprising:*

*establishing the extent of the first region by the amount of heat conducted from the liquid in the reservoir and the extent of contraction of the tissue resulting from expansion of the reservoir.*

*86. A method as defined in claim 84, also used to therapeutically heat treat a bladder neck which surrounds the prostatic urethra extending from the urinary bladder to increase the size of the urine drainage passage, further comprising:*

*directly contacting the bladder neck with the reservoir;*

*compressing the bladder neck sufficiently to reduce blood flow from the bladder neck; and*

*conducting sufficient heat from the liquid to heat the bladder neck therapeutically immediately adjoining the expanded reservoir to enlarge the urine drainage passage through the bladder neck.*

*87. A method as defined in claim 86, further comprising:*

*conducting sufficient heat from the liquid to coagulate at least a portion of the bladder neck adjoining the expanded reservoir.*

*88. A method as defined in claim 84, further comprising:*

*conducting sufficient heat from the liquid to coagulate tissue in the first region.*

*89. A method as defined in claim 88, further comprising:*

*emitting sufficient electromagnetic radiation from the antenna to coagulate tissue in the second region.*

*90. A method as defined in claim 84, further comprising:*

*emitting sufficient electromagnetic radiation from the antenna to coagulate tissue in the second region.*

*91. A method as defined in claim 84, further comprising:*

*heating therapeutically the tissue in the first and second regions to create a shell of tissue surrounding the expanded urine drainage passage.*

*92. A method as defined in claim 84, further comprising:*

*heating therapeutically the tissue in the first and second regions to create a stent from tissue surrounding the expanded urine drainage passage.*

*93. A method a defined in claim 84, further comprising:*

*heating therapeutically the tissue in the first and second regions to destroy sufficient tissue to create a cavity within the remaining tissue which forms the expanded urine drainage passage.*

*94. A method as defined in claim 84, further comprising:*

*heating the liquid in the reservoir to a temperature of at least 60 degrees Celsius.*

*95. A method as defined in claim 84, further comprising:*

*defusing medicine from the fluid reservoir to the tissue contacting the reservoir.*

*96. A method as defined in claim 84, further comprising:*

*adding additional heat to the liquid beyond that heat absorbed from the antenna and from the emitted electromagnetic radiation.*

*97. A method as defined in claim 96, further comprising:*

*adding the additional heat within the expandable reservoir.*

*98. A method as defined in claim 97, wherein:*

*the catheter used comprises an electrically energized heat source within the expandable reservoir, the electrically energized heat source being separate from the antenna, the catheter also comprising a feed cable extending from a position exterior of the urethra within the catheter and connecting to the antenna and to the heat source to conduct energy to the antenna and to the heat*

*source, the feed cable emitting heat as a result of conducting energy to the antenna, the catheter also comprising a cooling channel extending along the feed cable;*

*conducting energy to the antenna and to the heat source through the feed cable;*

*conducting liquid through the cooling channel to remove heat from the feed cable caused by conducting the energy to the antenna; and*

*protecting the urethra and the tissue surrounding the feed cable from heat from the feed cable.*

*99. A method as defined in claim 98, further comprising:*

*measuring the temperature of the liquid in the reservoir;*

*measuring the temperature of the prostate in the second region; and*

*separately controlling the relative amounts of energy delivered to the antenna and to the heat source relative to the measured temperatures of the liquid in the reservoir and of the tissue in the second region, respectively.*

*100. A method as defined in claim 84, wherein:*

*the catheter used comprises a feed cable extending from a position exterior of the urethra within the catheter and connecting to the antenna to conduct energy to the antenna, the feed cable emitting heat as a result of conducting energy to the antenna, the catheter also comprising a cooling channel extending along the feed cable; and the method further comprises:*

*conducting energy to the antenna through the feed cable;*

*conducting liquid through the cooling channel to remove heat from the feed cable caused by conducting the energy to the antenna; and*

*protecting the urethra and the tissue surrounding the feed cable from heat from the feed cable.*

*101. A method as defined in claim 98 or 100, wherein:*

*the catheter used further comprises a channel extending from a position exterior of the urethra within the catheter and communicating with the reservoir; and the method further comprises:*

*filling the reservoir with liquid through the channel; and*

*pressurizing the liquid within the reservoir by applying pressure through the channel.*

*102. A method as defined in claim 101, further comprising:*

*separating the liquid conducted in the cooling channel from the liquid in the channel communicating with the reservoir.*

*103. A method as defined in claim 101, further comprising:*

*containing the liquid in the reservoir separately from the liquid in cooling channel.*

*104. A method as defined in claim 84, further comprising:*

*positioning a liquid temperature sensor within the reservoir to sense the temperature of liquid within the reservoir.*

*105. A method as defined in claim 84, further comprising:*

*positioning a tissue temperature sensor in the prostate to sense the temperature of the tissue surrounding the reservoir.*

*106. A method as defined in claim 105, wherein:*

*the catheter used comprises a carrier moveably positioned within the catheter to extend from the catheter and penetrate into the prostate at a distance from the reservoir, the tissue temperature sensor connected to the carrier to contact the penetrated prostate upon extending the carrier from the catheter;*

*penetrating the carrier into the prostate; and*

*measuring the temperature of the prostate with the tissue temperature sensor connected to the carrier at a distance from the reservoir.*

*107. A method as defined in claim 106, further comprising:*

*measuring the temperature of the prostate tissue in the second region with the tissue temperature sensor.*

*108. A method as defined in claim 107, wherein:*

*the catheter used comprises a plurality of the tissue temperature sensors positioned on the carrier; and*

*penetrating the carrier into the prostate to position the plurality of tissue temperature sensors to measure the temperature of the prostate at a plurality of different distances from the reservoir.*

* * * * *